United States Patent
Fournier et al.

(10) Patent No.: US 11,686,684 B2
(45) Date of Patent: Jun. 27, 2023

(54) RAMAN SPECTROSCOPY BASED ASSAY FOR BOTH LOW AND HIGH ABUNDANT BIOMOLECULES IN A BIOLOGICAL FLUID SAMPLE

(71) Applicant: CytoVeris Inc., Farmington, CT (US)

(72) Inventors: David Fournier, Northborough, MA (US); Rishikesh Pandey, Unionville, CT (US)

(73) Assignee: CytoVeris, Inc., Farmington, CT (US)

( * ) Notice: Subject to any disclaimer, the term of this patent is extended or adjusted under 35 U.S.C. 154(b) by 0 days.

(21) Appl. No.: 17/513,824

(22) Filed: Oct. 28, 2021

(65) Prior Publication Data

US 2022/0128477 A1   Apr. 28, 2022

Related U.S. Application Data

(60) Provisional application No. 63/106,534, filed on Oct. 28, 2020.

(51) Int. Cl.
*G01N 21/65* (2006.01)
*A61B 5/00* (2006.01)
*G01N 33/543* (2006.01)
*G01J 3/44* (2006.01)

(52) U.S. Cl.
CPC ......... *G01N 21/658* (2013.01); *A61B 5/0075* (2013.01); *G01J 3/4412* (2013.01); *G01N 33/54346* (2013.01)

(58) Field of Classification Search
None
See application file for complete search history.

(56) References Cited

U.S. PATENT DOCUMENTS

2013/0065777 A1 *   3/2013   Altug ............... G01N 33/54346
                                                     506/16

FOREIGN PATENT DOCUMENTS

WO    WO-2020176793 A1 *   9/2020   ......... G01N 15/0612

OTHER PUBLICATIONS

7. Homola, J., et al. "Multi-analyte surface plasmon resonance biosensing." Methods 37.1 (2005): 26-36 (Year: 2005).*

(Continued)

*Primary Examiner* — Tarifur R Chowdhury
*Assistant Examiner* — Roberto Fabian, Jr.
(74) *Attorney, Agent, or Firm* — Getz Balich LLC

(57) ABSTRACT

A system and method for assaying high and low abundant biomolecules within a biological fluid sample is provided. The method includes: a) placing a biological fluid sample in contact with a first nanostructure surface; b) interrogating the sample with a light source, the sample in contact with the first nanostructure surface, the interrogation using a SERS technique; c) detecting an enhanced Raman scattering from at least one high abundant biomolecule type and producing first signals representative thereof; d) placing the sample in contact with a second nanostructure surface having a targeting agent that targets a low abundant biomolecule; e) interrogating the sample with the light source using the SERS technique; f) detecting the enhanced Raman scattering from the low abundant biomolecules and producing second signals representative thereof; and g) assaying the biological fluid sample using the first signals and the second signals.

21 Claims, 4 Drawing Sheets

(56) References Cited

OTHER PUBLICATIONS

C. Zhang et al., "Coherent Raman Scattering Microscopy in Biology and Medicine", Annu Rev Biomed Eng 17, 415-445 (2015).
H. Kneipp et al., "SERS—a single-molecule and nanoscale tool for bioanalytics", Chemical Society Reviews 37, 1052-1060 (2008).
M. D. Morris et al., "Resonance Raman Spectroscopy", Analytical Chemistry 51, 182A-192A (1979).
M. Li et al., "Multiplexed detection of serological cancer markers with plasmon-enhanced Raman spectro-immunoassay", Chem Sci 6, 3906-3914 (2015).
N. Feliu et al., "SERS Quantification and Characterization of Proteins and Other Biomolecules", Langmuir 33, 9711-9730 (2017).
R. Dong et al., "Detection and Direct Readout of Drugs in Human Urine Using Dynamic Surface-Enhanced Raman Spectroscopy and Support Vector Machines", Analytical Chemistry 87, 2937-2944 (2015).
R.C. Prince et al., "Stimulated Raman Scattering: From Bulk to Nano", Chemical Reviews 117, 5070-5094 (2017).
S. Nie et al., "Probing Single Molecules and Single Nanoparticles by Surface-Enhanced Raman Scattering", Science 275, 1102-1106 (1997).
S. Tanwar et al., "Advancing Raman spectroscopy from research to clinic: Translational potential and challenges" Spectrochim Acta A Mol Biomol Spectrosc 260, 119957 (2021).
V. D'Elia et al., "Analysis of street cocaine samples in nasal fluid by Raman spectroscopy", Taianta 154, 367-373 (2016).
X. Li et al., "Spectral analysis of human saliva for detection of lung cancer using surface-enhanced Raman spectroscopy", Journal of Biomedical Optics 17, 037003 (2012).
Z. Huang et al., "Label-free Optical Spectroscopy Platform for Diagnosis of Heparin-Induced Thrombocytopenia", Angew Chem Int ed Engl 59, 5972-5978 (2020).

* cited by examiner

RAMAN SPECTROSCOPY BASED ASSAY FOR BOTH LOW AND HIGH ABUNDANT BIOMOLECULES IN A BIOLOGICAL FLUID SAMPLE

This application claims priority to U.S. Patent Appln. No. 63/106,534 filed Oct. 28, 2020, which is hereby incorporated by reference in its entirety.

BACKGROUND OF THE INVENTION

1. Technical Area

The present disclosure relates to a combined biomolecule analyzer for measuring both low and high abundance biomolecules in the same fluid sample such as serum, semen, interstitial fluid, middle ear fluid, saliva, urine, whole blood, or any bodily fluid using surface enhanced Raman scattering (SERS).

2. Background Information

Raman spectroscopy is widely used as a method of material and compound identification in industries such as the bio-pharmaceutical industry, chemical and petrochemical sectors, security/screening, authentication, biomedical etc. The spectral signatures observed using Raman spectroscopy arise due to the excitation of vibrational frequencies that are specific to a given chemical bond, and the optical spectrum observed in what is known as the Raman spectrum. It has been used for identification and quantification of biomolecules including proteins, lipids, glucose etc. [1]

While Raman spectroscopy provides molecular fingerprinting information, only one in about one hundred million (1 in ~$10^8$) photons are inelastically scattered. This typically results in a lower signal-to-noise ratio or often necessitates a long signal acquisition time. Several approaches have been employed to enhance intrinsically weak Raman signals and thereby increase the detection sensitivity of Raman spectroscopy. These approaches include resonance Raman [2], Surface-enhanced Raman scattering (SERS) [3], coherent anti-Stokes Raman scattering (CARS) [4], and stimulated Raman scattering (SRS) [5].

Surface enhanced Raman Spectroscopy (SERS) addresses the problem of low sensitivity of Raman signal by enhancing the Raman scattering of analytes adsorbed on nanostructures due to the excitation of the localized surface plasmons. SERS analysis is attractive for biomolecule (e.g., protein) identification and quantification, as it offers quantitative enhancement of the signal with facile readout with highly multiplexing capability. SERS has also been harnessed for the label-free detection of biomarkers in various body fluids, such as blood plasma [6], urine [7], saliva [8], and nasal fluid [9]. In addition to label-free detection, SERS has also been used for a targeted detection using antibodies for protein quantification [10] including multiplexed detection [11]. SERS has been shown to show ultrasensitive detection up to single molecular detection [12].

What is needed is a composite biomolecule assay that can be used for detection and quantification of both high-abundant and low abundant biomolecules in the same biological sample.

SUMMARY OF THE INVENTION

According to an aspect of the present disclosure, a method for assaying one or more high abundant biomolecules and one or more low abundant biomolecules within a biological fluid sample is provided. The method includes: a) placing a biological fluid sample in contact with a first nanostructure surface; b) interrogating the biological fluid sample with a light source, the biological fluid sample in contact with the first nanostructure surface, the interrogation using a surface enhanced Raman spectroscopic (SERS) technique configured to produce an enhanced Raman scattering from at least one of one or more high abundant biomolecules adsorbed on the first nanostructure surface; c) detecting the enhanced Raman scattering from at least one of the one or more high abundant biomolecules using a light detector configured to produce first signals representative of the enhanced Raman scattering from the at least one of the one or more high abundant biomolecules; d) placing the biological fluid sample in contact with at least one second nanostructure surface, the at least one second nanostructure surface functionalized with at least one targeting agent configured to target at least one or the one or more low abundant biomolecules; e) interrogating the biological fluid sample with the light source, the biological fluid sample in contact with the at least one second nanostructure surface, the interrogation using the SERS technique configured to produce an enhanced Raman scattering from at least one of the one or more low abundant biomolecules captured by the at least one targeting agent functionalized on the at least one second nanostructure surface; f) detecting the enhanced Raman scattering from the one or more low abundant biomolecules and producing second signals representative thereof; and g) assaying the biological fluid sample using the first signals and the second signals.

In any of the aspects or embodiments described above and herein, the step of assaying the biological fluid sample may include determining the presence of the at least one of the one or more high abundant biomolecules and determining the presence of the at least one or the one or more low abundant biomolecules.

In any of the aspects or embodiments described above and herein, the step of assaying the biological fluid sample may include determining a quantity of the at least one of the one or more high abundant biomolecules present within the biological fluid sample.

In any of the aspects or embodiments described above and herein, the step of assaying the biological fluid sample may include determining a quantity of the at least one of the one or more low abundant biomolecules present within the biological fluid sample.

In any of the aspects or embodiments described above and herein, the step of interrogating the biological fluid sample in contact with the at least one second nanostructure surface and the step of detecting the enhanced Raman scattering from the one or more low abundant biomolecules may be performed after the step of interrogating the biological fluid sample in contact with the at least one first nanostructure surface and the step of detecting the enhanced Raman scattering from the one or more high abundant biomolecules.

In any of the aspects or embodiments described above and herein, the at least one second nanostructure surface may include a first serial nanostructure surface and a second serial nanostructure surface arranged in series, the at least one targeting agent may include a first targeting agent and a second targeting agent, and the first serial nanostructure surface may be functionalized with the first targeting agent and the second serial nanostructure surface may be functionalized with the second targeting agent.

In any of the aspects or embodiments described above and herein, the at least one second nanostructure surface may include a plurality of targeting regions and the at least one targeting agent may include a plurality of targeting agents different from one another, and each said targeting region of the plurality of targeting regions may be functionalized with at least one of the different targeting agents.

In any of the aspects or embodiments described above and herein, each of the plurality of targeting agents may be selective to a different type of biomolecule.

In any of the aspects or embodiments described above and herein, the at least one second nanostructure surface may be functionalized with a single targeting agent configured to selectively target one type of the low abundant biomolecules.

According to an aspect of the present disclosure, a method for assaying a biological fluid sample is provided. The method includes: a) placing a biological fluid sample in contact with a first nanostructure surface free of any biomolecule targeting agents; b) interrogating a biological fluid sample in contact with the first nanostructure surface with a light source, the interrogation using a surface enhanced Raman spectroscopic (SERS) technique configured to produce an enhanced Raman scattering from at least one type of high abundant biomolecule present within the fluid sample adsorbed on the first nanostructure surface; c) detecting the enhanced Raman scattering from the at least one type of high abundant biomolecule using a light detector configured to produce first signals representative of the enhanced Raman scattering from the at least one type of high abundant biomolecule; d) placing the biological fluid sample in contact with at least one second nanostructure surface, the at least one second nanostructure surface functionalized with at least one targeting agent configured to target at least one type of low abundant biomolecule; e) interrogating the biological fluid sample in contact with the at least one second nanostructure surface with the light source, the interrogation configured to produce Raman scattering from the at least one type of low abundant biomolecule captured by the at least one targeting agent functionalized on the at least one second nanostructure surface; f) detecting the Raman scattering from the at least one type of low abundant biomolecule and producing second signals representative thereof; and g) assaying the biological fluid sample using the first signals and the second signals.

According to an aspect of the present disclosure, a system for assaying a biological fluid sample is provided that includes a first nanostructure, at least one second nanostructure, a light source, a light detector, and a system controller. The first nanostructure surface is free of biomolecular targeting agents. The at least one second nanostructure surface is functionalized with at least one targeting agent configured to target at least one type of low abundant biomolecule within the fluid sample. The system controller is in communication with the light source, the light detector, and a memory storing instructions, which instructions when executed cause the processor to: a) control the light source to interrogate the biological fluid sample disposed in contact with the first nanostructure surface with a beam of light, wherein the interrogation is part of a surface enhanced Raman spectroscopic (SERS) technique configured to produce an enhanced Raman scattering from at least one type of high abundant biomolecule present within the fluid sample and adsorbed on the first nanostructure surface; b) control the light detector to detect the enhanced Raman scattering from the at least one type of high abundant biomolecule and produce first signals representative of the enhanced Raman scattering from the at least one type of high abundant biomolecule present within the fluid sample; c) control the light source to interrogate the biological fluid sample disposed in contact with the at least one second nanostructure surface with a beam of light, wherein the interrogation is part of a SERS technique configured to produce an enhanced Raman scattering from the at least one type of low abundant biomolecule within the fluid sample and captured by the at least one targeting agent functionalized on the at least one second nanostructure surface; d) control the light detector to detect the enhanced Raman scattering from the captured at least one type of low abundant biomolecule within the fluid sample and produce second signals representative thereof; and e) assay the biological fluid sample using the first signals and the second signals.

In any of the aspects or embodiments described above and herein, the system may be configured to move the biological fluid sample through a microfluidic device such that the biological fluid sample encounters the first nanostructure surface prior to encountering the at least one second nanostructure surface.

In any of the aspects or embodiments described above and herein, the instructions when executed may cause the processor to control the light source to interrogate the biological fluid sample in contact with the first nanostructure surface prior to interrogating the biological fluid sample in contact with the at least one second nanostructure surface.

In any of the aspects or embodiments described above and herein, the instructions when executed may cause the processor to determine the presence of at least one of the at least one type of high abundant biomolecule or the at least one type of low abundant biomolecule within the fluid sample.

In any of the aspects or embodiments described above and herein, the instructions when executed may cause the processor to determine a quantity of the at least one type of high abundant biomolecule within the fluid sample.

In any of the aspects or embodiments described above and herein, the instructions when executed may cause the processor to determine a quantity of the at least one type of low abundant biomolecule within the fluid sample.

In any of the aspects or embodiments described above and herein, the at least one second nanostructure surface may include a first serial nanostructure surface and a second serial nanostructure surface arranged in series, the at least one targeting agent may include a first targeting agent and a second targeting agent, and the first serial nanostructure surface may be functionalized with the first targeting agent and the second serial nanostructure surface may be functionalized with the second targeting agent.

In any of the aspects or embodiments described above and herein, the at least one second nanostructure surface may include a plurality of targeting regions and the at least one targeting agent may include a plurality of targeting agents different from one another, and each said targeting region of the plurality of targeting regions may be functionalized with at least one of the different targeting agents.

In any of the aspects or embodiments described above and herein, each of the plurality of targeting agents may be selective to a different type of biomolecule.

In any of the aspects or embodiments described above and herein, the at least one second nanostructure surface may be functionalized with a single targeting agent configured to selectively target one type of the low abundant biomolecules.

In any of the aspects or embodiments described above and herein, the system may further include a dispersive element operable to separate wavelengths of the enhanced Raman scattering from the at least one type of high abundant biomolecule or the enhanced Raman scattering from the at least one type of low abundant biomolecule, or both.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DISCLOSURE

The present disclosure includes a method and system 20 for performing an analysis of biomolecules (e.g., proteins) that may be present within a bodily fluid sample such as blood serum, blood plasma, urine, saliva, nasal fluid, and the like. Aspects of the present disclosure permit a passive analysis of the fluid sample that can be used to determine the presence of a particular biomolecule with the fluid sample, and if present, information regarding the quantity/concentration of the biomolecule within the fluid sample. The presence and the concentration of the biomolecule can be used for variety of applications such as but not limited to disease diagnosis both at early and late states, disease staging, therapeutic monitoring, therapeutic intervention, and the like. These aspects of the present disclosure utilize a surface enhanced Raman spectroscopic ("SERS") process that uses a SERS nanostructure surface to significantly improve the ability of the system 20 to detect Raman signals from a biomolecule of interest. The exact mechanism of the SERS enhancement effect is presently debated; i.e., the enhancement effect is either an electromagnetic effect or a chemical effect. For purposes of describing the present disclosure, we will describe the SEAS enhancement effect in terms as an electromagnetic effect.

Figure 3:
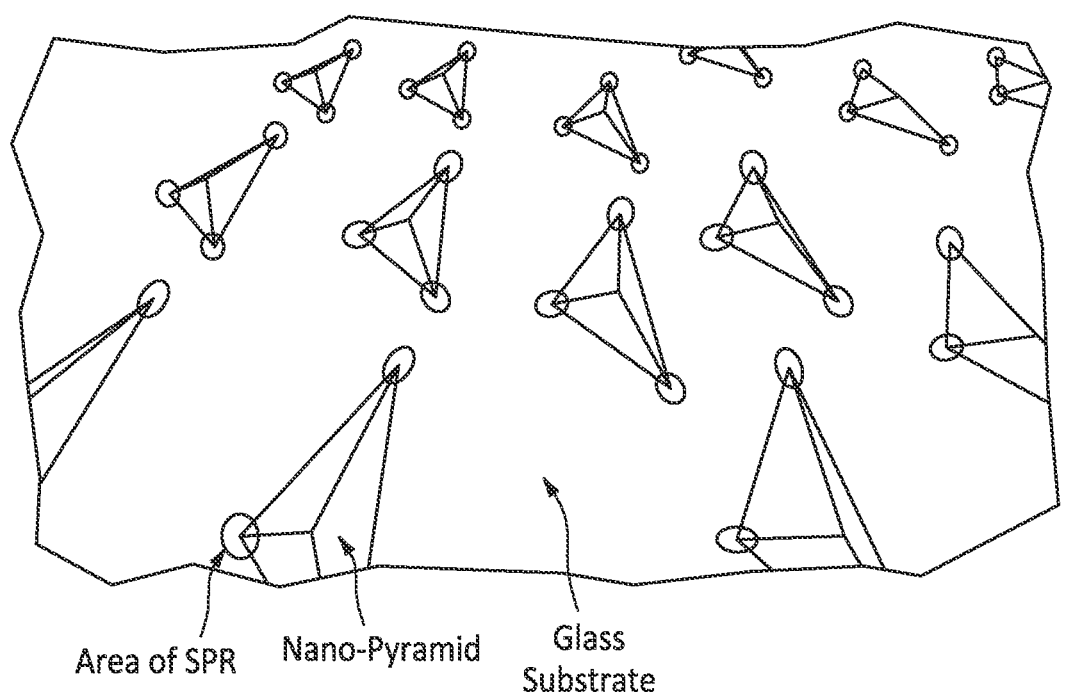
FIG. 3 is a schematic representation of a nanostructure surface having an array of nanopyramids.

Regarding the present disclosure, the SERS enhancement effect may be described as an increase in intensity of the Raman signal produced by a biomolecule as a result of "interaction" of the biomolecule with the SERS-active substrate subjected to an excitation light. According to the electromagnetic theory, the Raman signal enhancement effect occurs because of an enhancement in the electric field provided by the SERS-active substrate. When an excitation light strikes the surface of the SERS-active substrate, localized surface plasmons are excited and those surface plasmons in turn substantially enhance the Raman scattering signal of the biomolecule; e.g., by orders of magnitude. The enhancement produced by the surface plasmons is greatest when the surface of the SERS substrate is roughened or includes arrangements of nanoparticles. To facilitate the description herein the aforesaid roughened or otherwise prepared SERS substrate surface will hereinafter be referred to as a "nanostructure surface 22". The SERS nanostructure surface 22 may be produced by a variety of different techniques including, but not limited to etching, lithography, etc. SERS nanostructure surfaces 22 may be configured with geometric features designed to enhance the production of surface plasmons; e.g., geometric features like nanopyramids, nanoprisms, nanostars, and the like. These geometric features typically have multiple sharp edges that produce areas of surface plasmon resonance ("SPR") upon excitation; i.e., pursuant to the electromagnetic effect theory, these are areas of strong electromagnetic fields that facilitate enhancement of the Raman signal from the analyte in the vicinity of sharp nanotips. A SERS nanostructure surface 22 will include many such areas that produce enhanced plasmonic response. FIG. 3 diagrammatically illustrates a SERS nanostructure surface 22 having nanopyramid geometric features and areas where SPR is understood to be enhanced.

The type of material used in the SERS nanostructure surface 22 is selected to produce a plasmonic response when subjected to the excitation light. The SERS effect has been demonstrated in metals such as gold (Au) and silver (Ag), as well as platinum (Pt), ruthenium (Ru), palladium (Pd), iron (Fe), cobalt (Co), nickel (Ni), copper (Cu), and the like or combinations thereof. However, the SERS enhancement effect is much stronger when the SERS nanostructure surface 22 comprises a coinage material (e.g., Au, Ag, Pt, etc.), or combinations thereof. The present disclosure is not limited to using any particular SERS nanostructure material.

A biomolecule having a Raman signal response that may be enhanced via a SERS effect may be described as being "adsorbed" onto the SERS nanostructure surface 22. As used herein, a biomolecule "adsorbed" onto a SERS nanostructure surface 22 may be in contact with the surface 22 or may be sufficiently close to be able to participate in SERS enhancement. In this sense, the SERS enhancement effect may be described as affecting only a very small fraction of sample volume contiguous with or in the vicinity of strong SERS-active regions such as tips of the surface 22. Consequently, the biomolecules which will not come into the vicinity of the nanotips will very likely not participate in strong SERS enhancement. Considering the interaction volume of the nanotip and with appropriate dilution of the bodily fluid, the SERS detection will be from a single molecule at a time. Those biomolecules not participating in SERS enhancement will likely be of no value in the analysis of the fluid sample; e.g., their signal-to-noise ratio is too low to produce meaningful information.

Figure 1:
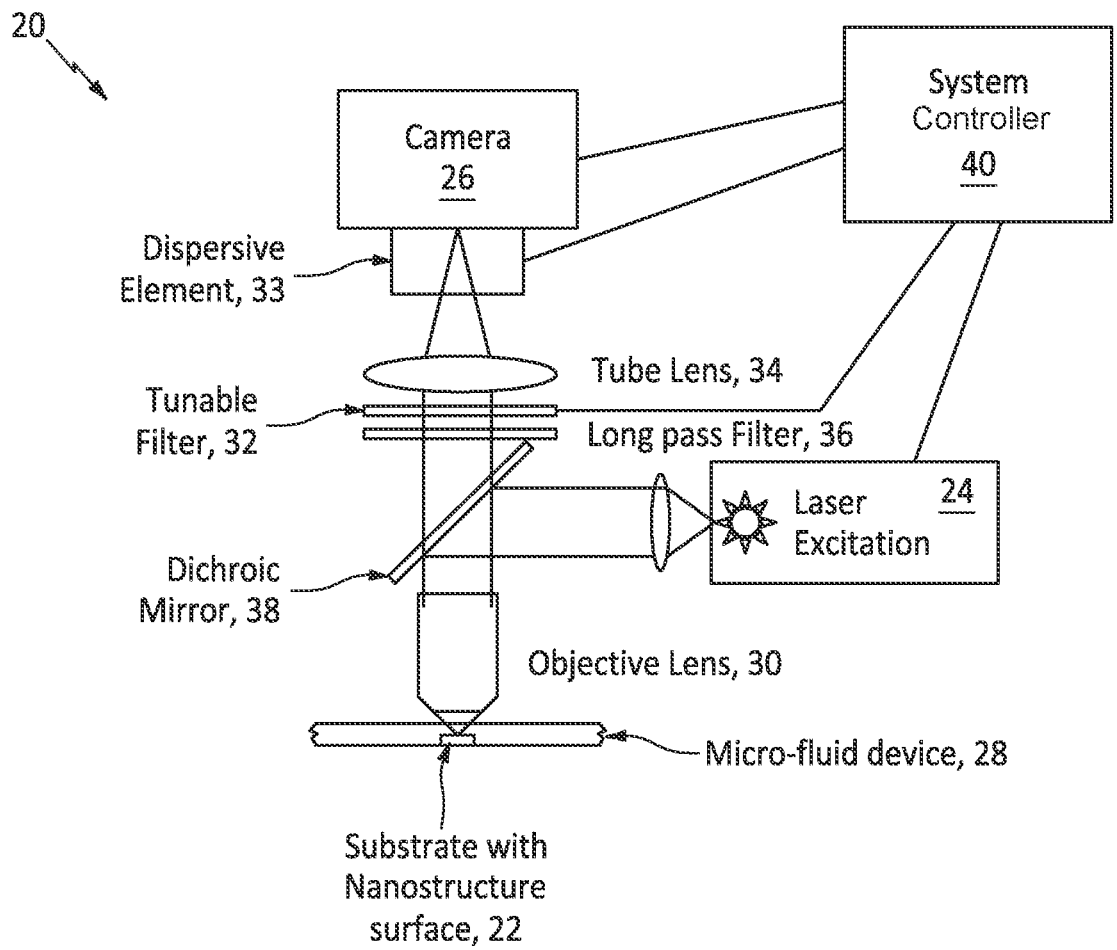
FIG. 1 is a schematic illustrating a present disclosure SERS-based detection apparatus embodiment.

A non-limiting example of a present disclosure system 20 is shown in FIG. 1. The system 20 includes a light source 24, a light detector 26, a microfluidic device 28, an objective lens 30, a tunable filter (e.g., a Fabry-Perot filter) 32, a dispersive element 33, a tube lens 34, a long pass filter 36, a dichroic mirror 38, and a system controller 40.

The light source 24 is configured to emit coherent light and an example of an acceptable light source 24 is a laser. Non-limiting examples of acceptable laser types include solid state, gas, diode laser or vertical-cavity surface-emitting lasers (VCSELs). The present disclosure may utilize coherent light at a variety of different wavelengths, and the light source 24 is therefore not limited to coherent light at any particular wavelength or wavelength band.

The light detector 26 is configured to receive light (e.g., Raman spectra) emitted from the interrogated fluid sample and produce signals representative thereof. The signals produced by the light detector 26 are transferred to the system controller 40. Non-limiting examples of light detectors 26 include light sensors that convert light energy into an electrical signal such as a camera, a simple photodiode, a CCD array, or the like. In some embodiments, only the light detector 26 can be configured to achieve spectrally-resolved information without use of any dispersive element 33 or tunable filter 32.

The tunable filter 32 may be controllable to alternately permit passage of different wavelength bands of light. As an alternative to a tunable filter 32, the present disclosure may utilize a plurality of different band pass filters to produce different wavelength limited filtered light.

The dispersive element 33 separates the wavelengths of scattered Raman light and facilitates optical dispersion of the collected light into different spectral components based on the wavelengths of the component light. Non-limiting examples of a dispersive element include a diffraction grating, a prism, a colloidal crystal array, and the like.

The system controller 40 is in communication with other system 20 components such as the light source 24, light detector 26, the tunable filter 32, the dispersive element 33, and the like. The system controller 40 may be in communication with one or more of these components to control the operation of the component and/or to receive signals from that component to perform the functions described herein. The system controller 40 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 20 to accomplish the same algorithmically and/or coordination of system components. The system controller 40 includes or is in communication with one or more memory devices. The present disclosure is not limited to any particular type of memory device, and the memory device may store instructions and/or data in a non-transitory manner. Examples of memory devices that may be used include read-only memory, random access memory, volatile memory, non-volatile memory, static memory, dynamic memory, flash memory, cache memory, and/or any device that stores digital information. The system controller 40 may include, or may be in communication with, an input device that enables a user to enter data and/or instructions, and may include, or be in communication with, an output device configured, for example to display information (e.g., a visual display or a printer), or to transfer data, etc. Communications between the system controller 40 and other system components may be via a hardwire connection or via a wireless connection.

In the system 20 example shown in FIG. 1, excitation light produced by the light source 24 is directed against the dichroic mirror 38 and is redirected to be received by an objective lens 30. The excitation light passes through the objective lens 30 and is incident to the fluid sample in communication with a microfluidic device 28 having a SERS nanostructure surface 22 aligned with the objective lens 30. The microfluidic device 28 is configured to contain the fluid sample as it is in contact with and/or as it passes by the nanostructure surface 22. The SERS nanostructure surface 22 may be part of a substrate that is disposed within the microfluidic device 28 or an integral surface of the microfluidic device 28. Either way, the microfluidic device 28 is configured such that the fluid sample is in communication with the SERS nanostructure surface 22. The backscattered light that includes Raman scattering light produced by the excitation light incident to the fluid sample is collected up through the objective lens 30 and passes through the dichroic mirror 38. After passing through the dichroic mirror 38, the collected light may pass through optical elements (e.g., the long pass filter 36, the tunable filter 32, the tube lens 34, the dispersive element 33) that filter out the excitation light and disperse the collected Raman scattering light. The collected and processed Raman scattering light is detected by the light detector 26 (shown as a camera in FIG. 1) and the light detector 26 produces signals representative thereof and communicates the same to the system controller 40.

To be clear, the system 20 embodiment shown in FIG. 1 and described above is a non-limiting example provided for the purpose of describing functionality of the system 20 described herein.

The low-abundance detection system is performed after the high-abundance measurement from the same sample and does not require a microfluidic device. However, the same SERS system shown in the FIG. 1 can be used for low-abundant detection without a microfluidic channel.

Figure 2:
FIG. 2 is a schematic illustrating a present disclosure SERS-based biomolecule detection method.

Aspects of the present disclosure methodology may utilize SERS to produce high spatial resolution spectroscopic images of different nanostructure surfaces 22 in a two-step process. As schematically shown in FIG. 2, a fluid sample may be subjected to a two-step process capable of providing information regarding the presence of one or more biomolecules in a fluid sample in instances when a biomolecule of interest is in high abundance within the fluid sample (i.e., a relatively high concentration) and/or when a biomolecule of interest is in low abundance (i.e., low relative concentration). For purposes of describing the present disclosure, the term "in high abundance" means biomolecule concentrations in the range of millimolar to micromolar, and the term "in low abundance" means biomolecule concentrations below micromolar.

In the first step of the method (or first subsystem 20 of the system 20), the presence of particular biomolecules within the fluid sample can be determined based on the Raman scattered light produced as a result of excitation light being applied to a fluid sample in communication with the SERS nanostructure surface 22 disposed in the microfluidic device 28. As indicated above, Raman scattered light that has not been SERS enhanced has a very low signal-to-noise ratio and therefore is essentially noise. Hence, those biomolecules that are not adsorbed by the SERS nanostructure surface 22 (i.e., not in contact with a SERS nanostructure surface 22 or not sufficiently close to be able to participate SERS enhancement) produce little or no useful biomolecule information. As best understood, any unenhanced Raman scattered light produced by biomolecules away from SERS nanostructure surface 22 will not interfere with the enhanced Raman scattering light signal. Significantly, the enhanced Raman scattered light produced from biomolecules within the fluid sample that are "adsorbed" by SERS nanostructure surface 22 can produce useful information; e.g., presence and quantity.

Of course, a fluid sample may contain a number of different biomolecules, each of which has a unique Raman signature for a given excitation wavelength. The present system 20 may be configured to produce information on a select one or more of those biomolecules by filtering the collected Raman scattering light. The system 20 may be configured to process the collected Raman scattered light in a variety of different ways (e.g., via stored instructions). For example, in some embodiments the system 20 may collect the Raman scattering light and bin similar Raman scattering light signals (e.g., "signatures") together. Artificial intelligence, machine learning, or any other data analytical tool can be used to determine similarities. Those collected alike Raman scattering light signals may then be further processed to ascertain the presence and in some instances the quantity of the biomolecule within the fluid sample associated with that particular Raman signature. That processing may analyze the biomolecules of the fluid sample by correlating the collected Raman scattering signal to empirical data relating to known biomolecules. Based on that correlation the biomolecule presence and quantity may be determined. In an alternative method, the system 20 may collect the Raman scattering light and bin all of the collected Raman scattering light signals (e.g., "signatures") together. Afterward, the collective signals may subsequently be subjected to a decomposition process to determine the presence and quantity of one or more biomolecules within the fluid sample; e.g., decompose the Raman scattering light into portions associated with distinct Raman scattering signatures that may be associated with a known biomolecule. The above two examples are provided to illustrate the utility of the present disclosure and therefore the present is not limited to these examples.

A high spatial resolution Raman "image" of the signals generated at the surface 22 from the flowing untargeted high-abundant protein allows "counting" of areas with Raman spectra correlating to specific molecules, thus allowing the determination of concentration through Poisson statistics.

The unique Raman scattering light "signatures" of biomolecules at the SERS nanostructure surface 22 can be decoded to identify different biomolecule types (e.g., different protein types) expected to be present in the fluid sample at abundances proportional to the concentration in the fluid. The adsorption and desorption kinetics of the biomolecules onto and off of the SERS nanostructure surface 22 is statistically driven, and depend on factors including but not limited to binding energies, temperature, etc. These factors can be modeled to allow interpretation of the relative biomolecule concentrations from the Raman signatures observed via an algorithm utilized by the system controller 40 (e.g., stored algorithmic instructions) tuned to detect the Raman signatures of different biomolecules.

Figure 4A:
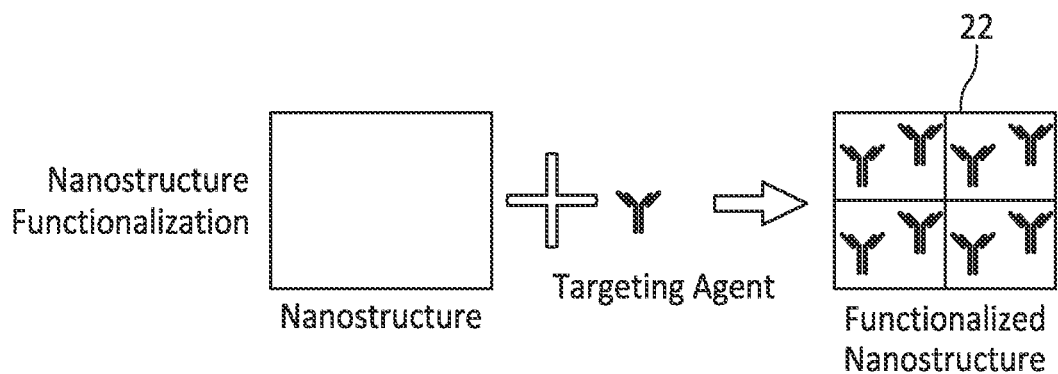
FIG. 4A is a schematic of a low-abundance targeted protein detection method embodiment illustrating a nanostructure functionalization.
Figure 4B:
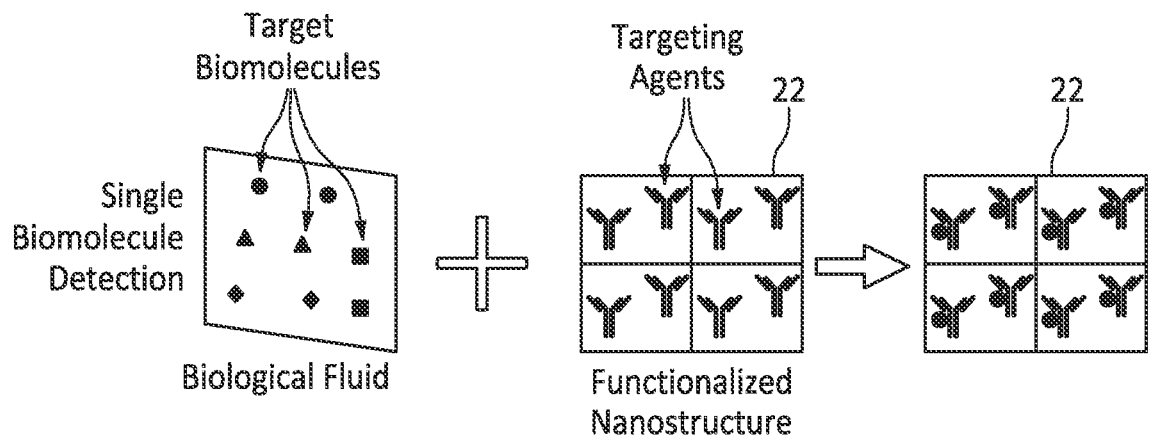
FIG. 4B is a schematic of a low-abundance biomolecule detection method embodiment using a nanostructure functionalized to capture a single type of biomolecule.
Figure 4C:
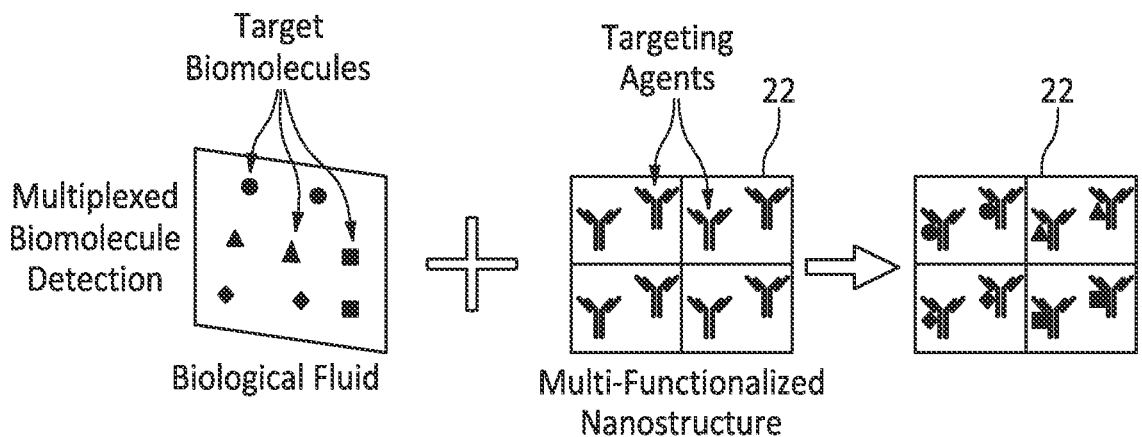
FIG. 4C is a schematic of a low-abundance biomolecule detection method embodiment using a nanostructure functionalized to capture multiple types of biomolecules.

The second step of the methodology (or subsystem 20 of the system 20) is directed to analyzing the fluid sample for the presence/quantity of biomolecules that are in low abundance within the fluid sample. This step of the present disclosure includes using SERS to produce high spatial resolution spectroscopic images of different nanostructure surfaces 22 configured to target low abundance biomolecules. An example of a targeted detection may involve using one or more "functionalized" SERS nanostructure surfaces 22. As shown in FIG. 4A, a nanostructure surface 22 may be functionalized by adding a targeting agent to the nanostructure surface 22. A variety of targeting agents may be used including but not limited to antibodies, aptamers, affibodies, synthetic antibody scaffolds, and the like. As shown in FIGS. 4B and 4C, a nanostructure surface 22 may be functionalized with a targeting agent designed to capture a single type of biomolecule (FIG. 4B), or a nanostructure surface 22 may be functionalized with a plurality of different targeting agents to capture a plurality of different types of biomolecules (FIG. 4C).

A conventional "sandwich" type immunoassay involves exposing a surface coated with binding sites (e.g., a capture antibody) to a fluid sample potentially containing target molecules. A solution containing detection molecules (e.g., a detection antibody that includes a colorimetric molecule) is subsequently added. The detection molecules are allowed to bind to the target molecules and provide the mechanism for identifying the target molecules. Such an assay requires multiple steps and time to perform.

The present disclosure method, in contrast, does not use a detection molecule. Rather, detection of the target biomolecule may be performed using Raman spectrum analysis; e.g., the presence of the target biomolecule is confirmed if the Raman spectrum analysis reveals the presence of the Raman signature of the target biomolecule. Referring to FIG. 4B, the method permits the detection of a single biomolecule; e.g., a nanostructure surface 22 functionalized with a target agent that is specific to a single type of biomolecule. Referring to FIG. 4C, the method permits the detection of a plurality of different biomolecules; e.g., a multi-functionalized nanostructure surface 22 configured with a plurality of different target agents, with each target agent specific to a respective target biomolecule. As schematically shown in FIGS. 4A-4C, a nanostructure surface 22 may be sectioned with different surface regions having different target agents specific to different biomolecules of interest. In addition to using the Raman intensity of the biomolecule for identification purposes, one can also utilize the shift in the wavenumber peak position to quantitate the biomolecule.

The present disclosure combination approach of two steps or two subsystems is configured to allow analysis of biomolecule concentrations in the range of about or greater than millimolar to sub-femtomolar with sensitivity and specificity similar to that of ELISA sandwich assays. In fact, the present disclosure method is understood to provide improved sensitivity over prior art assay techniques and is also immune to photobleaching.

Figure 5:
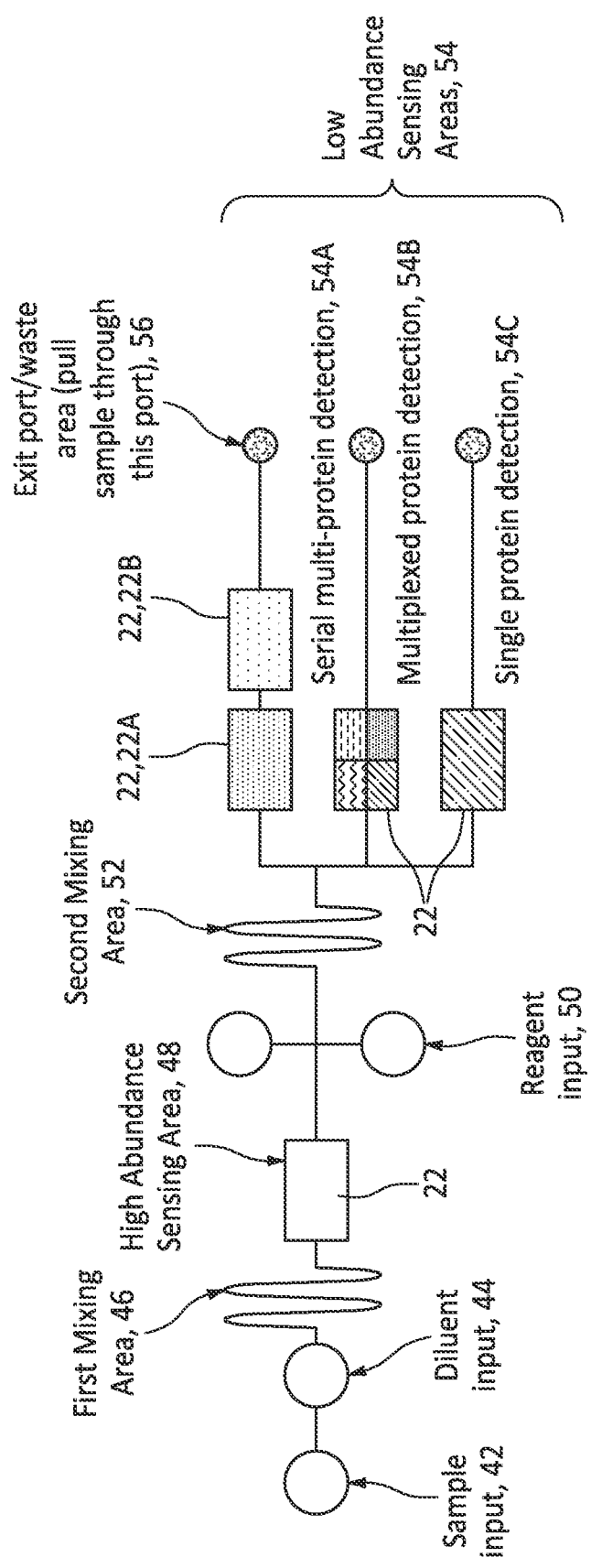
FIG. 5 is a schematic diagram of a present disclosure embodiment that includes both high-abundance and low-abundance biomolecule detection from the same sample.

FIG. 5 diagrammatically illustrates an embodiment of the present disclosure having a high-abundance biomolecule sensing area followed by multiple targeted low-abundance sensing areas. More specifically, FIG. 5 illustrates a sample input 42, a diluent input 44, a first mixing area 46, a high abundance sensing area 48, a reagent input 50, a second mixing area 52, and a low abundance sensing area 54 that includes: a) a serial multi-protein (biomolecule) detection lane 54A; b) a multiplexed protein (biomolecule) detection lane 54B; and c) a single protein (biomolecule) detection lane 54C. A fluid sample deposited into the sample input 42 is passed to the diluent input 44. The addition of a diluent may not be required in certain cases. The fluid sample (diluted or undiluted) is then passed into the first mixing area 46. If diluent was added to the fluid sample, the first mixing area 46 will ensure the diluted sample is uniformly mixed. The fluid sample is then passed into and through the high abundance sensing area 48. As described above, the high abundance sensing area 48 includes a nanostructure surface 22 that is placed in communication with the fluid sample. Biomolecules within the fluid sample that are adsorbed by SERS nanostructure surface 22 produce enhanced Raman scattered light when interrogated by excitation light. The collected Raman scattering light is collected and analyzed to provide useful information (e.g., presence and quantity) relating to the biomolecules in high abundance within the fluid sample. The fluid sample is then passed through the reagent input 50 and the second mixing area 52. The addition of one or more reagents is not required. If a reagent is added to the fluid sample, the second mixing area 52 will ensure the combined sample and reagent are uniformly mixed. Beyond the second mixing area 52, a portion of the fluid sample enters one or more low abundance sensing areas 54A, 54B, 54C configured to sense for biomolecules that are in low abundance within the fluid sample; e.g., low abundance sensing areas 54A, 54B, 54C that include one or more nanostructure surfaces 22 functionalized with one or more target agents each specific to a single type of biomolecule. In the system 20 diagrammatically shown in FIG. 5, the low abundance area 54 includes a serial multi-protein (biomolecule) detection lane 54A, a multiplexed protein (biomolecule) detection lane 54B, and a single protein (biomolecule) detection lane 54C. The serial multi-protein (biomolecule) detection lane 54A includes a first nanostructure surface 22A configured to detect a first type of protein and a second nanostructure surface 22B in series configured to detect a second type of protein. The first type of protein is detected as the fluid sample communicates with the first nanostructure surface 22A. The fluid sample continues and passes through to the second nanostructure surface 22B to detect the second type of protein. In the multiplexed protein (biomolecule) detection lane 54B, a nanostructure surface 22 having a four different detection regions (each shown with a different pattern) is disposed to receive a portion of the fluid sample. Each nanostructure surface 22 detection region is configured to detect a different type of protein. In the single protein detection lane 54C, a nanostructure surface 22 configured to detect a single protein is disposed to receive a portion of the fluid sample. Beyond the respective nanostructure surfaces 22 in each detection lane, an exit port/waste area 56 is disposed to receive the fluid sample that has passed through the respective nanostructure surface 22. The system 20 is configured to detect the respective targeted biomolecules/proteins using the SERS nanostructure surfaces 22 to produce high spatial resolution spectroscopic images that can be subsequently analyzed to detect the targeted biomolecules that are low in abundance within the fluid sample.

Hence, aspects of the present disclosure provides a single system 20 operable to measure biomolecule concentrations in an over millimolar to femtomolar range with relevant accuracy/sensitivity/specificity through the entire range. Raman signatures allow the determination of biomolecules through the inelastic scattering of light with the biomolecules. The SERS technique used in the present disclosure acquires (~10^5) amplified data over a very small region at the nanostructure surface 22 from undiluted or an appropriately diluted sample, making the measurements inherently a function of single molecules at a given time in the flow process. As a result, Raman scattering signals collected from this surface 22 can be interpreted as coming from individual molecules in the vicinity of functionalized strong SERS-active regions of the surface 22. A high spatial resolution Raman "image" of the signals generated at the surface 22 allows "counting" of areas with Raman spectra correlating to specific molecules, thus allowing the determination of concentration of low abundant molecules through Poisson statistics.

The low abundant biomolecule detection strategy is similar to the high-abundant biomolecule detection strategy except the former uses a targeting agent to capture specific biomolecules.

The present disclosure's use of a nanostructure surface 22 that enables a determination of biomolecules directly from concentration without collecting the biomolecules allows measurement of high abundance biomolecules to be made without interfering with low abundance biomolecules. Importantly, this aspect allows the "capture" section (i.e., the low abundance detection areas using targeting agents) to take biomolecules out of the fluid sample solution, without interference from the upstream high abundance measurement subsystem 20.

While the principles of the disclosure have been described above in connection with specific apparatuses and methods, it is to be clearly understood that this description is made only by way of example and not as limitation on the scope of the disclosure. Specific details are given in the above description to provide a thorough understanding of the embodiments. However, it is understood that the embodiments may be practiced without these specific details.

It is noted that the embodiments may be described as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements unless the context clearly indicates otherwise. As used herein, "comprises" means "includes." Thus, "comprising A or B," means "including A or B, or A and B," without excluding additional elements.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. Any reference to attached, fixed, connected or the like may include permanent, removable, temporary, partial, full and/or any other possible attachment option.

No element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprise", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements may be described as individual units and shown as independent of one another to facilitate the description. In alternative embodiments, such elements may be configured as combined elements.

REFERENCES

The following references are hereby incorporated by reference in their respective entireties:
1. S. Tanwar et al., "Advancing Raman spectroscopy from research to clinic: Translational potential and challenges"; Spectrochim Acta A Mol Biomol Spectrosc 260, 119957 (2021).
2. M. D. Morris et al., "Resonance Raman Spectroscopy", Analytical Chemistry 51, 182A-192A (1979).
3. H. Kneipp et al., "SERS—a single-molecule and nanoscale tool for bioanalytics", Chemical Society Reviews 37, 1052-1060 (2008)
4. C. Zhang et al., "Coherent Raman Scattering Microscopy in Biology and Medicine", Annu Rev Biomed Eng 17, 415-445 (2015).
5. R. C. Prince et al., "Stimulated Raman Scattering: From Bulk to Nano", Chemical Reviews 117, 5070-5094 (2017).
6. Z. Huang et al., "Label-free Optical Spectroscopy Platform for Diagnosis of Heparin-Induced Thrombocytopenia", Angew Chem Int ed Engl 59, 5972-5978 (2020).
7. R. Dong et al., "Detection and Direct Readout of Drugs in Human Urine Using Dynamic Surface-Enhanced Raman Spectroscopy and Support Vector Machines", Analytical Chemistry 87, 2937-2944 (2015).
8. X. Li et al., "Spectral analysis of human saliva for detection of lung cancer using surface-enhanced Raman spectroscopy", Journal of Biomedical Optics 17, 037003 (2012).
9. V. D'Elia et al., "Analysis of street cocaine samples in nasal fluid by Raman spectroscopy", Talanta 154, 367-373 (2016).
10. N. Feliu et al., "SERS Quantification and Characterization of Proteins and Other Biomolecules", Langmuir 33, 9711-9730 (2017).
11. M. Li et al., "Multiplexed detection of serological cancer markers with plasmon-enhanced Raman spectro-immunoassay", Chem Sci 6, 3906-3914 (2015).
12. S. Nie et al., "Probing Single Molecules and Single Nanoparticles by Surface-Enhanced Raman Scattering", Science 275, 1102-1106 (1997).

The invention claimed is:
1. A method for assaying one or more high abundant biomolecules and one or more low abundant biomolecules within a biological fluid sample, comprising:
   placing a biological fluid sample in contact with a first nanostructure surface;
   interrogating the biological fluid sample with a light source, the biological fluid sample in contact with the first nanostructure surface, the interrogation using a surface enhanced Raman spectroscopic (SERS) technique configured to produce an enhanced Raman scattering from at least one of one or more high abundant biomolecules adsorbed on the first nanostructure surface;
   detecting the enhanced Raman scattering from at least one of the one or more high abundant biomolecules using a light detector configured to produce first signals representative of the enhanced Raman scattering from the at least one of the one or more high abundant biomolecules;
   placing the biological fluid sample in contact with at least one second nanostructure surface, the at least one second nanostructure surface functionalized with at least one targeting agent configured to target at least one or the one or more low abundant biomolecules;
   interrogating the biological fluid sample with the light source, the biological fluid sample in contact with the at least one second nanostructure surface, the interrogation using the SERS technique configured to produce an enhanced Raman scattering from at least one of the one or more low abundant biomolecules captured by the at least one targeting agent functionalized on the at least one second nanostructure surface;
   detecting the enhanced Raman scattering from the one or more low abundant biomolecules and producing second signals representative thereof;
   assaying the biological fluid sample using the first signals and the second signals.

2. The method of claim 1, wherein the step of assaying the biological fluid sample includes determining the presence of the at least one of the one or more high abundant biomolecules and determining the presence of the at least one or the one or more low abundant biomolecules.

3. The method of claim 2, wherein the step of assaying the biological fluid sample includes determining a quantity of the at least one of the one or more high abundant biomolecules present within the biological fluid sample.

4. The method of claim 2, wherein the step of assaying the biological fluid sample includes determining a quantity of the at least one of the one or more low abundant biomolecules present within the biological fluid sample.

5. The method of claim 1, wherein the step of interrogating the biological fluid sample in contact with the at least one second nanostructure surface and the step of detecting the enhanced Raman scattering from the one or more low abundant biomolecules is performed after the step of interrogating the biological fluid sample in contact with the at least one first nanostructure surface and the step of detecting the enhanced Raman scattering from the one or more high abundant biomolecules.

6. The method of claim 1, wherein the at least one second nanostructure surface includes a first serial nanostructure surface and a second serial nanostructure surface arranged in series, the at least one targeting agent includes a first targeting agent and a second targeting agent, and the first serial nanostructure surface is functionalized with the first targeting agent and the second serial nanostructure surface is functionalized with the second targeting agent.

7. The method of claim 1, wherein the at least one second nanostructure surface includes a plurality of targeting regions and the at least one targeting agent includes a plurality of targeting agents different from one another, and each said targeting region of the plurality of targeting regions is functionalized with at least one of the different targeting agents.

8. The method of claim 7, wherein each of the plurality of targeting agents is selective to a different type of biomolecule.

9. The method of claim 1, wherein the at least one second nanostructure surface is functionalized with a single targeting agent configured to selectively target one type of said low abundant biomolecules.

10. A method for assaying a biological fluid sample, comprising:
   placing a biological fluid sample in contact with a first nanostructure surface free of any biomolecule targeting agents;
   interrogating a biological fluid sample in contact with the first nanostructure surface with a light source, the interrogation using a surface enhanced Raman spectroscopic (SERS) technique configured to produce an enhanced Raman scattering from at least one type of high abundant biomolecule present within the biological fluid sample adsorbed on the first nanostructure surface;
   detecting the enhanced Raman scattering from the at least one type of high abundant biomolecule using a light detector configured to produce first signals representative of the enhanced Raman scattering from the at least one type of high abundant biomolecule;
   placing the biological fluid sample in contact with at least one second nanostructure surface, the at least one second nanostructure surface functionalized with at least one targeting agent configured to target at least one type of low abundant biomolecule;
   interrogating the biological fluid sample in contact with the at least one second nanostructure surface with the light source, the interrogation configured to produce Raman scattering from the at least one type of low abundant biomolecule captured by the at least one targeting agent functionalized on the at least one second nanostructure surface;
   detecting the Raman scattering from the at least one type of low abundant biomolecule and producing second signals representative thereof;
   assaying the biological fluid sample using the first signals and the second signals.

11. A system for assaying a biological fluid sample, comprising:
   a first nanostructure surface free of biomolecular targeting agents;
   at least one second nanostructure surface functionalized with at least one targeting agent configured to target at least one type of low abundant biomolecule within the biological fluid sample;
   a light source;
   a light detector;
   a system controller in communication with the light source, the light detector, and a memory storing instructions, which instructions when executed cause a processor to:
      control the light source to interrogate the biological fluid sample disposed in contact with the first nanostructure surface with a beam of light, wherein the interrogation is part of a surface enhanced Raman spectroscopic (SERS) technique configured to produce an enhanced Raman scattering from at least one type of high abundant biomolecule present within the biological fluid sample and adsorbed on the first nanostructure surface;
      control the light detector to detect the enhanced Raman scattering from the at least one type of high abundant biomolecule and produce first signals representative of the enhanced Raman scattering from the at least one type of high abundant biomolecule present within the biological fluid sample;
      control the light source to interrogate the biological fluid sample disposed in contact with the at least one second nanostructure surface with a beam of light, wherein the interrogation is part of a SERS technique configured to produce an enhanced Raman scattering from the at least one type of low abundant biomolecule within the biological fluid sample and captured by the at least one targeting agent functionalized on the at least one second nanostructure surface;
      control the light detector to detect the enhanced Raman scattering from the captured at least one type of low abundant biomolecule within the biological fluid sample and produce second signals representative thereof;
      assay the biological fluid sample using the first signals and the second signals.

12. The system of claim 11, wherein the system is configured to move the biological fluid sample through a microfluidic device such that the biological fluid sample encounters the first nanostructure surface prior to encountering the at least one second nanostructure surface.

13. The system of claim 12, wherein the instructions when executed cause the processor to control the light source to interrogate the biological fluid sample in contact with the first nanostructure surface prior to interrogating the biological fluid sample in contact with the at least one second nanostructure surface.

14. The system of claim 11, wherein the instructions when executed cause the processor to determine the presence of at least one of the at least one type of high abundant biomolecule or the at least one type of low abundant biomolecule within the biological fluid sample.

15. The system of claim 14, wherein the instructions when executed cause the processor to determine a quantity of the at least one type of high abundant biomolecule within the biological fluid sample.

16. The system of claim 14, wherein the instructions when executed cause the processor to determine a quantity of the at least one type of low abundant biomolecule within the biological fluid sample.

17. The system of claim 11, wherein the at least one second nanostructure surface includes a first serial nanostructure surface and a second serial nanostructure surface arranged in series, the at least one targeting agent includes a first targeting agent and a second targeting agent, and the first serial nanostructure surface is functionalized with the first targeting agent and the second serial nanostructure surface is functionalized with the second targeting agent.

18. The system of claim 11, wherein the at least one second nanostructure surface includes a plurality of targeting regions and the at least one targeting agent includes a plurality of targeting agents different from one another, and each said targeting region of the plurality of targeting regions is functionalized with at least one of the different targeting agents.

19. The system of claim 18, wherein each of the plurality of targeting agents is selective to a different type of biomolecule.

20. The system of claim 11, wherein the at least one second nanostructure surface is functionalized with a single targeting agent configured to selectively target one type of said low abundant biomolecules.

21. The system of claim 11, further comprising a dispersive element operable to separate wavelengths of the enhanced Raman scattering from the at least one type of high abundant biomolecule or the enhanced Raman scattering from the at least one type of low abundant biomolecule, or both.

* * * * *